United States Patent
Mueller

(10) Patent No.: US 7,790,668 B2
(45) Date of Patent: Sep. 7, 2010

(54) 2-METHOXY-2,6-DIMETHYLOCTANAL AND ITS USE AS A FRAGRANCE INGREDIENT

(75) Inventor: Urs Mueller, Duebendorf (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 12/065,407

(22) PCT Filed: Sep. 15, 2006

(86) PCT No.: PCT/CH2006/000501

§ 371 (c)(1),
(2), (4) Date: Mar. 10, 2008

(87) PCT Pub. No.: WO2007/030967

PCT Pub. Date: Mar. 22, 2007

(65) Prior Publication Data

US 2008/0261860 A1  Oct. 23, 2008

(30) Foreign Application Priority Data

Sep. 16, 2005 (EP) .................................. 05020309

(51) Int. Cl.
*A61K 8/18* (2006.01)
*A61Q 13/00* (2006.01)
*C07F 15/00* (2006.01)
*C07C 47/00* (2006.01)

(52) U.S. Cl. .......................... 512/25; 568/300; 568/420

(58) Field of Classification Search ................... 512/25; 568/420, 300
See application file for complete search history.

(56) References Cited

U.S. PATENT DOCUMENTS 3,963,648 A * 6/1976 Jones et al. ................... 512/25
4,311,617 A * 1/1982 Ansari et al. .................. 512/27

* cited by examiner

Primary Examiner—Milton I Cano
Assistant Examiner—Aaron Greso
(74) Attorney, Agent, or Firm—Norris McLaughlin & Marcus, PA

(57) ABSTRACT

6-Methoxy-2,6-dimethyloctanal, a method of its production and fragrance compositions comprising it.

5 Claims, No Drawings

2-METHOXY-2,6-DIMETHYLOCTANAL AND ITS USE AS A FRAGRANCE INGREDIENT

This is an application filed under 35 USC 371 of PCT/CH2006/000501.

The present invention refers to 6-methoxy-2,6-dimethyloctanal having a marine, sea, ozone, green, fruity, citrus odour note, to a method of its production and fragrance compositions comprising it.

In the fragrance industry there is a constant demand for new compounds that enhance or improve on odour notes, or impart new odour notes. In particular odour notes associated with fresh aquatic environments (seashores, mountain lakes, etc.) have become popular in perfumery recently.

It has been found that 6-methoxy-2,6-dimethyloctanal, which has never been described in literature before, possesses organoleptic properties, which have been found useful and appreciated for the preparation of perfume, perfuming compositions and perfumed products. Surprisingly, it was found that the compound of the present invention compared to 6-methoxy-2,6-dimethyheptanal (Methoxymelonal™) is characterized by an about 2.5 times lower odour threshold concentration, although being structurally very close to 6-methoxy-2,6-dimethylheptanal. Whereas Methoxymelonal™ is reminiscent of woodiness, 6-methoxy-2,6-dimethyloctanal is more citrus and possesses brighter, cleaner and fresher odour notes.

The odour threshold concentration is defined as the lowest concentration of the vapour of an odorous material in the air which can be detected by smell. The concentration can be measured by standard methods known in the art by using either olfactometry means or sniff-bottles allowing panelists to smell the presented headspace.

It is the low odour threshold concentration of 6-methoxy-2,6-dimethyloctanal that allows the use of lower concentrations of this compound in fragrance compositions to achieve an olfactory effect.

Thus the present invention refers in one of its aspects to the use of 6-methoxy-2,6-dimethyloctanal as fragrance ingredient.

The compound of to the present invention contains two chiral centres, and as such may exist as a mixture of stereoisomers, or it may be resolved as isomerically pure forms.

Resolving stereoisomers adds to the complexity of manufacture and purification of these compounds, and so it is preferred to use 6-methoxy-2,6-dimethyloctanal as a mixture of its stereoisomers simply for economic reasons. However, if it is desired to prepare individual stereoisomers, this may be achieved according to methodology known in the art, e.g. preparative HPLC and GC or by stereoselective synthesis.

The compound of the present invention may be used in a broad range of fragrance applications, e.g. in any field of fine and functional perfumery, such as perfumes, household products, laundry products, body care products and cosmetics. The compound can be employed in widely varying amounts, depending upon the specific application and on the nature and quantity of other odorant ingredients. Quite generally it can be said that 6-methoxy-2,6-dimethyloctanal is a very powerful odorant and, therefore, effects may already be obtained at very low dosage, e.g. 0.01 weight percent. On the other side it can be used even at very high concentrations, if combined with the optimal partners. The preferred concentration varies between about 0.01 weight percent and about 15 weight percent, preferably between 0.1 and 5 weight percent based on the end product. However, these values are given only by way of example, since the experienced perfumer may also achieve effects or may create novel accords with lower or higher concentrations.

In one embodiment, 6-methoxy-2,6-dimethyloctanal may be employed in a shampoo in an amount of from 0.1 to 3 weight percent. In another embodiment, 6-methoxy-2,6-dimethyloctanal may be used in fine perfumery in amounts of from 0.1 to 20 weight percent, more preferably between 0.1 and 5 weight percent.

The compound of the present invention can be used for the creation of a very broad spectrum of fragrance compositions by admixing it with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art. Thus, to a fragrance composition of fruity/melon, citrus character, 6-methoxy-2,6-dimethyloctanal confers freshness and cleans up the harshness of the ozone/melon note.

The following list comprises examples of known odorant molecules, which may be combined with the compound of the present invention:

essential oils and extracts, e.g. tree moss absolute, basil oil, castoreum, costus root oil, myrtle oil, oak moss absolute, geranium oil, jasmin absolute, patchouli oil, rose oil, sandalwood oil, wormwood oil, lavender oil or ylang-ylang oil;

alkohols, e.g. citronellol, Ebanol™, eugenol, farnesol, geraniol, Super Muguet™, linalool, phenylethyl alcohol, Sandalore™, terpineol or Timberol™;

aldehydes and ketones, e.g. α-amylcinnamaldehyde, Georgywood hydroxycitronellal, Iso E Super®, Isoraldeine®, Hedione®, maltol, methyl cedryl ketone, methylionone or vanillin;

ethers and acetals, e.g. Ambrox™, geranyl methyl ether, rose oxide or Spirambrene™;

esters and lactones, e.g. benzyl acetate, cedryl acetate, γ-decalactone, Helvetolide®, γ-undecalactone or Vetivenyl acetate;

macrocycles, e.g. ambrettolide, ethylene brassylate or Exaltolide®;

heterocycles, e.g. isobutylchinoline.

The compound of the present invention may be employed into the fragrance application simply by directly mixing the fragrance composition with the fragrance application, or it may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or it may be chemically bonded to substrates, which are adapted to release 6-methoxy-2,6-dimethyloctanal upon application of an external stimulus such as light, enzyme, or the like, and then mixed with the application.

Thus, the invention additionally provides a method of manufacturing a fragrance application, comprising the incorporation of 6-methoxy-2,6-dimethyloctanal as a fragrance ingredient, either by directly admixing it to the application or by admixing a fragrance composition comprising 6-methoxy-2,6-dimethyloctanal, which may then be mixed to a fragrance application, using conventional techniques and methods.

As used herein, "fragrance application" means any product, such as fine fragrance, e.g. perfume and eau de toilette; household products, e.g. detergents for dishwasher, surface cleaner; laundry products, e.g. softener, bleach, detergent; body care products, e.g. shampoo, shower gel; cosmetics, e.g. deodorant, vanishing crème; and air fresheners, comprising an odorant. This list of products is given by way of illustration and is not to be regarded as being in any way limiting.

The invention is now further described with reference to the following non-limiting examples.

EXAMPLE 1

Syntheses of 6-methoxy-2,6-dimethyloctanal

A) 6-Methoxy-6-methyl-2-octanone

To 2 kg 6-methyl-oct-5-en-2-one in 4 l methanol was added 800 ml concentrated sulphuric acid at 3° C. over a period of 40 minutes. After further stirring for 5 h at room temperature, the solution was poured onto 8 kg of ice water and extracted with tert.-butyl methyl ether. The combined organic phases were washed with 20% $Na_2CO_3$ (200 ml) and concentrated NaCl solution (3×150 ml). After removal of the solvent, the residue was distilled over a 70 cm Sulzer column to give 840 g recovered starting material (boiling point: 72°-75° C./10 mm Hg) and 970 g 6-methoxy-6-methyl-2-octanone (bp.: 95°-98° C./10 Torr=13.3 mbar).

$^1$H-NMR (400 MHz, $CDCl_3$): δ 0.84 (t, J=7.6 Hz, 3H), 1.09 (s, 3H), 1.38-1.61 (m, 6H), 2.14 (s, 3H), 2.44 (t, J=7.2 Hz, 2H), 3.14 (s, 3H).

IR: 1715 $cm^{-1}$.

B) 3-(4-Methoxy-4-methyl-hexyl)-3-methyl-oxirane-2-carboxylic acid methyl ester 860 g 6-Methoxy-6-methyl-2-octanone, 4 l tert.-butyl methyl ether and 648 g methyl chloroacetate were cooled to 0° C. under a blanket of nitrogen. Under further cooling, 350 g sodium methoxide was added in 6 portions over 20 minutes. The mixture was then stirred at room temperature till no more consumption of the ketone was observed (GC). After cooling to 0° C., 1 l 5% acetic acid (w/w) was added and the phases were separated. The aqueous phase was extracted with tert.-butyl methyl ether (500 ml). The combined organic phases were washed with water, concentrated $KHCO_3$ solution, concentrated NaCl solution and dried over $MgSO_4$. The yellow oil which remained after the removal of the solvent was distilled over a small Vigreux-column to give 823 g of 3-(4-methoxy-4-methyl-hexyl)-3-methyl-oxirane-2-carboxylic acid methyl ester (mixture of isomers, boiling point: 115°-128°/0.3 Torr=0.399 mbar).

$^1$H-NMR (400 MHz, $CDCl_3$): δ 0.8-0.88 (m, 3H), 1.07-1.09 (m, 3H), 1.35-1.75 (m, 11H), 3.12-3.15 (m, 3H), 3.34-3.36 (m, 1H), 3.78 (s) and 3.79 (s, total 3H).

MS: 87 (100%)

C) 6-Methoxy-2,6-dimethyl-octanal 180 g Potassium hydroxide dissolved in 800 ml water was added over 2 h to 810 g 3-(4-methoxy-4-methyl-hexyl)-3-methyl-oxirane-2-carboxylic acid methyl ester at a temperature of 0° C. to 5° C. Then 36 g KOH dissolved in 150 ml water was added in portions till the colour change from orange to beige persisted. The mixture which had pH 11 was then acidified at 0° C. by the addition of HCl 32% (300 ml, added over 30 minutes), followed by diluted phosphoric acid till pH 3 was reached. The phases were separated and the aqueous phase extracted with tert.-butyl methyl ether. The combined organic phases were washed with concentrated NaCl solution prior to evaporating the solvent. The very viscous oil which remained (780 g) was added dropwise over a period of 3 h to 300 ml PEG 200 which was kept at 160° C. Thereby the product distilled off. After the addition, steam was injected for about 30 minutes to distil off any steam-volatile product. The two phases of the distillate were separated and the aqueous phase extracted with tert.-butyl methyl ether. The combined organic phases were washed with $KHCO_3$ and NaCl. Evaporation of the solvent afforded 380 g of a faintly yellow oil which was distilled over a 60 cm Sulzer column to give 338 g 6-methoxy-2,6-dimethyl-octanal (bp. 65°-66° C./0.3 Torr=0.399 mbar).

$^1$H-NMR (400 MHz, $CDCl_3$): δ 0.83 (t, J=7.6 Hz, 3H), 1.07 (s, 3H), 1.1 (d, J=7.2 Hz, 3H), 1.28-1.52 (m, 7H), 1.66-1.76 (m, 1H), 2.31-2.42 (m, 1H), 3.12 (s, 3H), 9.62 (d, J=1.6 Hz, 1H).

EXAMPLE 2

Odour Threshold Concentration by Using an Olfactometer

The olfactometer functions on the principle of a linear dilution of an odorant in a carrier gas. The quantity of odorant displaced depends on its vapour pressure and the carrier gas flow. A constant flow of nitrogen, regulated by a flow regulator, carries the odorant from a sample container to a mixing chamber. There, the carrier gas-odour mixture is diluted with odourless air. From the mixing chamber one part of the diluted odorous air is allowed to flow via a fused silica capillary to the sniffing funnel. The flow rate through the capillary, which determines the dosage of odorous air from the mixing chamber into the sniffing funnel, depends on the opening of the valve which can be regulated via PC from 1 to 256 ml in binary steps. The final dilution of the odorous air sample occurs in the glass funnel by flushing them permanently with odourless air at a flow rate of 8 L/min. Forced-choice triangle presentation is achieved by a special automated channel setting device where only in one position of a switch the odorant delivering capillary enters in the sniffing funnel, whereas in the two other positions the capillary is positioned outside the funnel and where the effluent is sucked away. After each trial the channel setting is changed automatically and in a random order. The concentration is calculated from the odorants vapour pressure and from the dilution ratios that were applied in the olfactometer, assuming that vapour saturation is achieved in the sample generator. As a control the concentration was by sampling a known volume from the capillary effluent into a headspace filter and then determined. The panelist starts sniffing at the olfactometer at a concentration level at which he perceives the odorant at medium intensity. After three correct answers in three consecutive trials (or four correct ones of five trials) at the same level, stimulus concentration is decreased by a factor of two to the next lower level, and so on, until the panelist has reached his threshold level.

Under identical conditions the odour threshold concentration for 6-methoxy-2,6-dimethyloctanal and 6-methoxy-2,6-dimethylheptanal was measured and compared by a group of 12 panelists. The sequence with which of the two compounds the panelist started smelling was alternated. Both compounds were measured on the same day and the following data were obtained:

| Compound | Odour threshold concentration [ng/L] geometric mean |
|---|---|
| 6-methoxy-2,6-dimethyloctanal | 0.78 |
| 6-methoxy-2,6-dimethylheptanal | 1.92 |

It can bee seen from the results that the compound of the present invention has a threshold which is 2.46 times lower compared to the compound of the prior art. Based on this, a significant advance is achieved because much smaller amounts of the claimed compounds is required to impart the same olfactory effect.

EXAMPLE 3

Floral Fragrance Composition

| | Parts per weight |
|---|---|
| Linalool (Givaudan) | 30 |
| Mayol (Firmenich) | 25 |
| Dihydry Ionone Beta (Givaudan) | 8 |
| Ionone Beta (Givaudan) | 8 |
| Cepionate (Methyl dihydrojasmonate) | 250 |
| Cyclohexal | 20 |
| Dihydro Farnesal (3,7,11-Trimethyl-6,10-dodecadienal) | 20 |
| Farnesol Synt. (3,7,11-trimethyldodeca-2,6,10-trien-1-ol) | 20 |
| cis-3-Hexenyl benzoate | 25 |
| cis-3-Hexenyl salicylate | 25 |
| Hydroxycitronellal Synt | 30 |
| Dimetol ® (2,6-Dimethyl-2-heptanol) | 8 |
| Hedione (Firmenich) | 300 |
| Musk Ketone (4'-tert-Butyl-2',6'-dimethyl-3',5'-dinitroacetophenone) | 4 |
| Cassis Base 345 FH (Compounded Perfumery Base, Firmenich) | 3 |
| Indolene (CAS 67860-00-8) at 10% in DPG | 12 |
| Allyl Amyl Glycolate at 10% in DPG | 2 |
| N 112 (4-(p-Hydroxyphenyl)-2-butanone) at 10% in DPG | 5 |
| Alpha Damascone at 10% in DPG | 8 |
| Ethyl Linalool | 25 |
| Citral dimethyl acetal | 2 |
| Jasmone Cis (CAS 488-10-8) at 10% in DPG | 5 |
| Galaxolide ® 50 IPM (1,3,4,6,7,8-hexahydro-4,6,6,7,8,8-hexamethyl-cyclopenta-gamma-2-benzopyran) | 20 |
| Phenoxanol ® (1-pentanol, 3-methyl-5-phenyl) | 3 |
| para-Cresyl Isobutyrate at 1% in DPG | 2 |
| Dipropylene Glycol (DPG) | 130 |

The addition of 10 parts of 6-methoxy-2,6-dimethyloctanal makes the above composition more natural, rounder and fresher. It gives also an exotic juicy connotation to this floral fruity flower note and also helps to develop an attractive airy-marine floral odour.

EXAMPLE 2

Masculine Fragrance Composition

| | Parts per weight |
|---|---|
| Allyl Amyl Glycolate | 1 |
| Ambrofix (Givaudan) | 2 |

-continued

| | Parts per weight |
|---|---|
| Benzyl salicylate | 100 |
| Citronellyl acetate | 2 |
| Alpha Damascone at 10% in DPG | 9 |
| Dihydromyrcenol | 10 |
| Dimethyl benzyl carbinyl acetate | 8 |
| Dimethyl benzyl carbinyl butyrate | 3 |
| Pharaone (2-Cyclohexyl-1,6-heptadien-3-one) at 10% in DPG | 8 |
| Geranyl acetate | 3 |
| Grapefruit Ess.. | 70 |
| Azurone (7-(3-Methylbutyl)-2H-1,5-benzodioxepin-3(4H)-one) at 1% in DPG | 2 |
| Habanolide ® (Oxacyclohexadecen-2-one) | 100 |
| Georgywood (cis-1-(1,2,3,4,5,6,7,8-Octahydro-1,2,8,8-tetramethyl-2-naphthalenyl)-ethanone) | 250 |
| cis-3-Hexenol | 3 |
| cis-3-Hexenyl acetate | 1 |
| cis-3-Hexenyl salicylate | 10 |
| Hexyl cinnamic aldehyde | 45 |
| Hedione ® (Cyclopentaneacetic acid, 3-oxo-2-pentyl-, methyl ester) | 150 |
| Citron Ess. Oil | 45 |
| Cyclohexal | 20 |
| Linalool | 15 |
| Linalyl acetate Synt. | 45 |
| Orange Ess. Oil | 25 |
| Oranger Cristals (1-(2Nnaphthalenyl)-ethanone) at 10% in DPG | 2 |
| Gardenol | 5 |
| Terpineol Pure | 3 |
| Cyclal C (2,4-Dimethylcyclohex-3-enecarbaldehyde) at 10% in DPG | 14 |
| Dipropylene Glycol (DPG) | 19 |

The addition of 30 parts of 6-methoxy-2,6-dimethyloctanal brings to the above composition freshness, liveliness and comfort. It brings also a fresh marine note from the top to the dry-down, enhancing the brightness of the top note and keeping a natural freshness to the woody musky dry-down.

The invention claimed is:

1. A compound 6-Methoxy-2,6-dimethyloctanal, exhibiting a marine, sea, ozone and green odor note.

2. A fragrance composition comprising 6-methoxy-2,6-dimethyloctanal which said 6-methoxy-2,6-dimethyloctanal exhibits an odor note selected from the group consisting of: marine, sea, ozone and green odor notes.

3. A fragrance application comprising 6-methoxy-2,6-dimethyloctanal which said 6-methoxy-2,6-dimethyloctanal exhibits an odor note selected from the group consisting of: marine, sea, ozone and green odor notes.

4. A fragrance application according to claim 3 wherein the fragrance application is selected from the group consisting of: a perfume, household product, laundry product, body care product and a cosmetic product.

5. A method of manufacturing a fragrance application, comprising the step of:

incorporating into said fragrance application 6-methoxy-2,6-dimethyloctanal exhibiting an odor note selected from the group consisting of: marine, sea, ozone and green odor notes.

* * * * *